(12) United States Patent
Tulkis et al.

(10) Patent No.: US 7,393,355 B2
(45) Date of Patent: Jul. 1, 2008

(54) FEMORAL GUIDE AND PIVOTING REAMER

(75) Inventors: Peter Tulkis, Florida, NY (US); Gregory E. Plaskon, Clifton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 402 days.

(21) Appl. No.: 10/357,786

(22) Filed: Feb. 4, 2003

(65) Prior Publication Data
US 2004/0153081 A1 Aug. 5, 2004

(51) Int. Cl.
*A61B 17/00* (2006.01)
(52) U.S. Cl. .......................................... 606/80; 600/96
(58) Field of Classification Search .................. 606/79, 606/80, 84, 85, 87, 89, 96, 98
See application file for complete search history.

(56) References Cited

U.S. PATENT DOCUMENTS

| | | | |
|---|---|---|---|
| 4,738,256 A | 4/1988 | Freeman et al. | |
| 4,770,660 A | 9/1988 | Averill | |
| 4,777,942 A * | 10/1988 | Frey et al. | 606/80 |
| 4,809,689 A | 3/1989 | Anapliotis | |
| 4,892,093 A | 1/1990 | Zarnowski et al. | |
| 5,047,033 A | 9/1991 | Fallin | |
| 5,053,037 A | 10/1991 | Lackey | |
| 5,133,772 A | 7/1992 | Hack et al. | |
| 5,342,363 A | 8/1994 | Richelsoph | |
| 5,342,366 A * | 8/1994 | Whiteside et al. | 606/86 |
| 5,387,218 A * | 2/1995 | Meswania | 606/80 |
| 5,403,320 A | 4/1995 | Lumen et al. | |
| 5,474,559 A | 12/1995 | Bertin et al. | |
| 5,496,324 A * | 3/1996 | Barnes | 606/79 |
| 5,527,316 A * | 6/1996 | Stone et al. | 606/80 |
| 5,540,694 A * | 7/1996 | DeCarlo et al. | 606/80 |
| 5,601,563 A | 2/1997 | Burke et al. | |
| 5,624,444 A | 4/1997 | Wixon et al. | |
| 5,653,714 A | 8/1997 | Dietz et al. | |
| 5,749,876 A | 5/1998 | Duvillier et al. | |
| 5,810,828 A * | 9/1998 | Lightman et al. | 606/80 |
| 5,810,831 A | 9/1998 | D'Antonio | |
| 5,830,216 A | 11/1998 | Insall et al. | |
| 5,908,423 A | 6/1999 | Kashubea et al. | |
| 6,077,270 A | 6/2000 | Katz | |
| 2001/0001121 A1 | 5/2001 | Lombardo et al. | |
| 2003/0187449 A1* | 10/2003 | McCleary et al. | 606/80 |

* cited by examiner

*Primary Examiner*—Bruce E. Snow
(74) *Attorney, Agent, or Firm*—Lerner, David, Littenberg, Krumholz & Mentlik, LLP

(57) ABSTRACT

An apparatus for preparing the femur of a patient to receive a prosthesis is disclosed. A support is mountable in the recess and is shaped for mounting the first insert on the support. The insert is shaped for guiding pivoting of a post in a direction for reaming the recess.

39 Claims, 16 Drawing Sheets

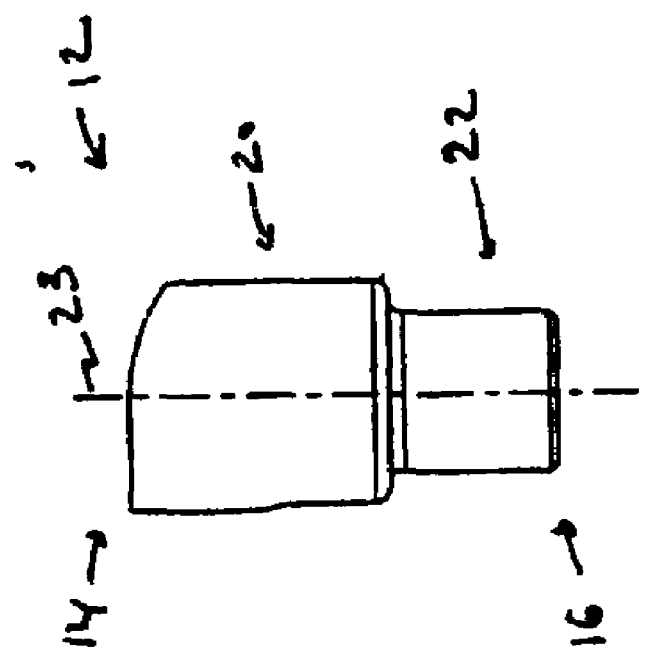
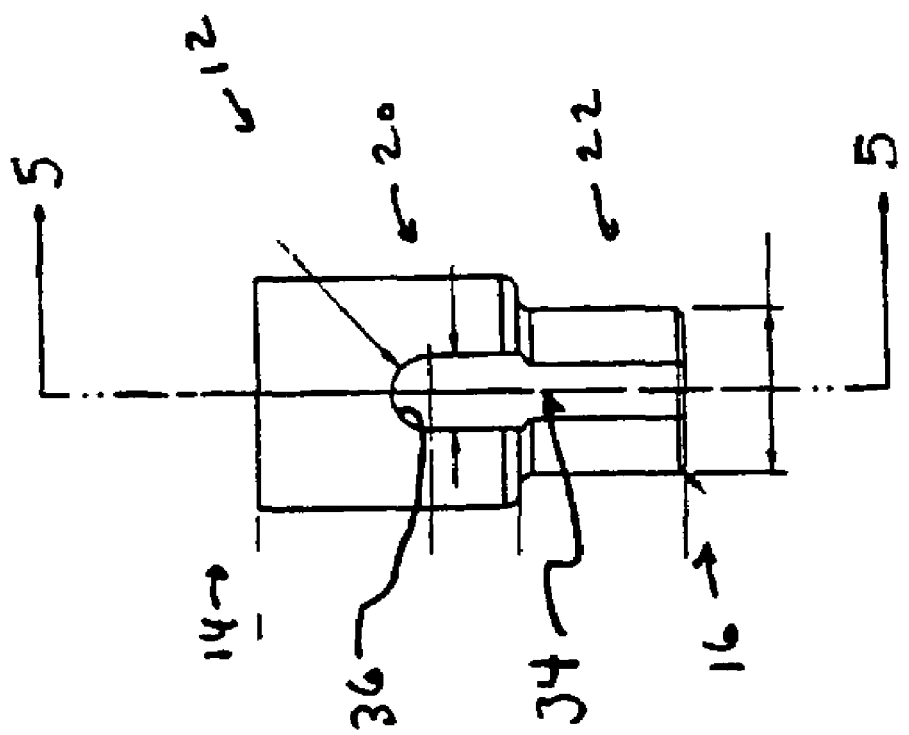

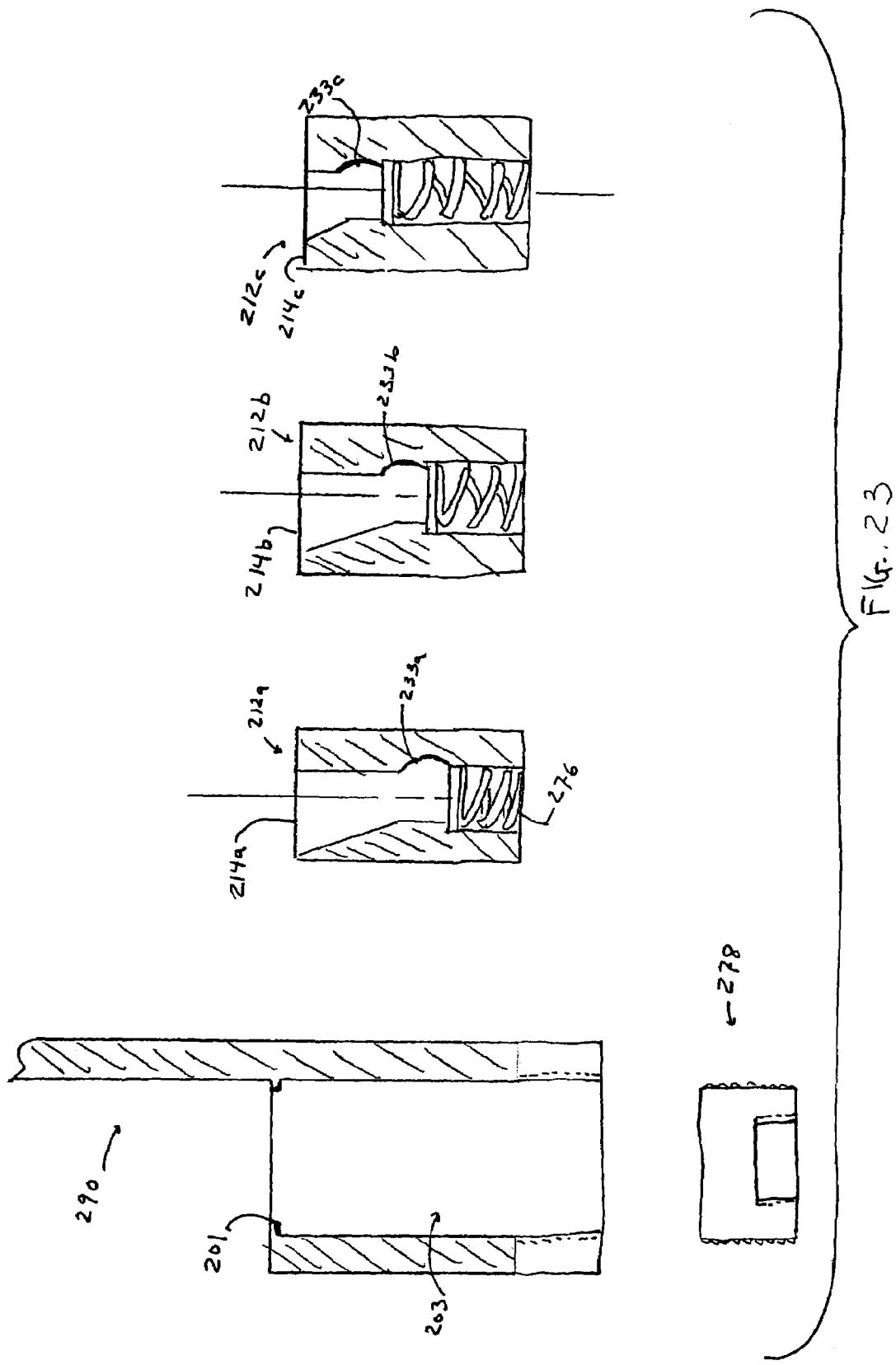

FEMORAL GUIDE AND PIVOTING REAMER

FIELD OF THE INVENTION

This invention generally relates to a method and apparatus for preparing a bone cavity for receiving a prosthesis. In particular, the invention relates to a surgical apparatus and method for shaping a cavity within a bone for receipt of a prosthesis for forming a joint in a patient's body.

BACKGROUND OF THE INVENTION

When installing a prosthesis for replacing a joint within the body, a portion of a bone is generally resected and a cavity is formed for receiving a prosthesis having a portion for forming a joint. A resection may be performed using a tool with a cutting edge, such as a chisel that is forced across an end of the bone to form a flat surface on which the prosthesis can transfer loads to the bone, or to remove a portion of bone that is damaged or deficient. A cavity is formed by a tool with a cutting edge driven longitudinally into the bone, such as a chisel, reamer or rasp. The cavity extends down the medulary canal and receives the stem of the prosthesis, which is used to provide some stability for the joint. In the implantation of a hip joint prosthesis, the head at the proximal end of the femur is removed and a hole is formed in the medullary canal of the femur. The cavity is then shaped so as to conform to the shape of the prosthesis selected by the surgeon according to the patient's indications.

Tools for shaping a cavity in a bone are known. A support having a guide arm for guiding a reamer in shaping a cavity in the femur is known. This apparatus requires a number of parts, including at least one guide arm which must be connected to an upper end of the guide body. A guide arm for the anterior side, as well as another guide arm for the posterior side must be attached to the upper end of the guide body, in order to shape both the anterior and posterior sides of the cavity. This apparatus complicates the method for shaping the cavity in the femur and includes many parts. Further, the guide arm allows the reamer to deviate from the path that produces the desired shape for the cavity. Another support has a guide bar that guides pivoting of a reamer. This system requires a plurality of supports and a multitude of reamers that correspond to different sized prostheses. Thus, the inventory of instruments is large and complicates preparation for, as well as the conduct of, the surgical procedure.

A plurality of different guide arms which can be selected according to the size of the prosthesis to be installed has also been proposed. However, this apparatus suffers from the drawbacks mentioned above.

A guide for shaping a cavity within an end of a bone for receiving a prosthesis, which simplifies the method of shaping the bone, is desirable. In addition, an apparatus that is adaptable according to the size of the prosthesis to be installed is also desired.

SUMMARY OF THE INVENTION

In a first aspect of the present invention, an apparatus for shaping a bone, comprises an insert shaped for guiding the pivoting of a shaping tool, and a support having an end adapted to be inserted into a cavity in the bone and having a mounting portion for mounting the insert on the support. The insert desirably guides pivoting of a shaping tool in a predetermined direction of the bone. The shaping tool may be carried on the insert. In certain embodiments, the insert has a connecting portion for connecting with the shaping tool.

Embodiments of the invention desirably include a plurality of inserts. Each insert is arranged to position the shaping tool in a different position as compared to the other inserts. The inserts enable the apparatus to be used to shape the bone for receiving any prosthesis, from a set of prostheses. For further flexibility, more than one support is provided and more than one insert is arranged for being assembled with each support. The insert desirably has a surface for guiding pivoting of the shaping tool.

The connecting portion of the first insert may comprise a post having an end and being assembled with the insert. In a preferred embodiment, the first insert has a bore defined therein and the bore is open on an upper end and a lower end of the insert and incorporating an engagement surface for engaging an end of the post and the post is received in the bore so that the post extends out the bore at the upper end of the insert.

In certain preferred embodiments, the insert has a top wall and a slot defined in the top wall. The first insert has a sidewall defining a bore in communication with the slot. The insert may have a central axis and the bore is desirably centered on the central axis. The slot extends in the top wall from the central axis to the sidewall of the insert. The slot and the bore may be offset from one another at a location and the bore may have an engagement surface at the location of the offset. The end of the post may have a shape corresponding to the shape of the engagement surface. In certain preferred embodiments, a fixing element is included for securing the end of the post in the insert.

In certain preferred embodiments, the insert comprises a first insert of a plurality of inserts. The insert is shaped for mounting on the support and for positioning the first insert with respect to the support. The apparatus desirably includes a second insert. In certain preferred embodiments, the first insert and the second insert are shaped for mounting on the support so that a shaping tool connected to the first insert has a position with respect to the support that is different from the position of the shaping tool connected to the second insert.

The support may have a body and the mounting portion may comprise a cavity defined by the body for receiving the insert. A longitudinally extending passage desirably communicates with the cavity. The body of the support may define an opening so that the passage is open at a front side of the support and so that the shaping tool may extend out the opening. The insert and the support are desirably shaped for positioning the insert and the shaping tool with respect to the support.

The lower end of the support is desirably shaped to be received in a cavity in a proximal end of a femur. In certain preferred embodiments, the support has an upper cylindrical portion and a lower conical portion. The lower conical portion may be shaped to correspond to a portion of a prosthesis to be inserted in the cavity. The conical portion of the support desirably positions the support within the bone.

The insert and the support are desirably shaped for locating the insert at a predetermined elevation with respect to the bone. The insert and the support are desirably shaped for locating the first insert with the respect to the bone so that the shaping tool pivots in a predetermined direction. A post is desirably assembled with the insert. A shaping tool is desirably shaped so as to be mounted on the post and to allow the shaping tool to rotate on the post. The shaping tool may comprise a reamer.

In certain preferred embodiments, the apparatus includes a post assembled with the insert, the insert has a central axis, and the post is pivotable between a first position and a second position.

In a further aspect of the present invention, a set of instruments for shaping a bone comprises a support to be mounted a cavity of the bone. The support has a mounting portion shaped for mounting an insert on the support. A first insert is shaped for guiding pivoting of a shaping tool and a second insert is shaped for guiding pivoting of a shaping tool. The first insert and the second insert are shaped for engagement with the support so that the first insert and second insert have different positions with respect to the bone. A set of instruments including a plurality of inserts having different positions with respect to the support may be mounted with a shaping tool for preparing the bone for receiving a prosthesis selected by the surgeon.

A further aspect of the present invention includes a method for shaping a bone comprising the steps of assembling an insert with a support. The insert carries a shaping tool. The support is inserted into a cavity in the bone, either before or after assembling the support and the insert, so as to position the shaping tool with respect to the bone.

In certain preferred embodiments, the insert is selected from a set of a plurality of inserts. The insert is desirably selected according to a desired position for shaping the bone. Each of the inserts of the plurality of inserts is desirably arranged so as to locate the shaping tool in a different position when the support is mounted in the cavity of the bone.

Desirably, the method includes selecting the insert according to a desired elevation. Each of the inserts is arranged so as to locate the shaping tool at a different elevation with respect to the bone. The support is, in certain preferred embodiments, shaped so as to locate the support at a desired elevation with respect to the bone for shaping the bone for a preselected prosthesis. The method includes positioning the insert with respect to the support so that the shaping tool pivots in a predetermined direction. The insert and the support are desirably positioned by adjusting the position of the insert with respect to the support until correspondingly shaped features of the insert and the support can be assembled with one another.

The method may include shaping the bone by pivoting the shaping tool in a predetermined direction of the bone. The insert is desirably shaped to guide the pivoting of the shaping tool.

The step of shaping desirably includes rotating the shaping tool so as to engage cutting surfaces of the shaping tool with the bone.

The method may further comprise rotating the support with respect to the bone, to position the shaping tool. The support may be positioned so that the shaping tool engages a desired portion of the bone.

BRIEF DESCRIPTION OF THE DRAWINGS

These and other features, aspects and advantages of the present invention will become better understood with regard to the following description, appended claims, and accompanying drawings where:

FIG. 3 is a left elevational view of a first insert in accordance with the embodiment of FIGS. 1 and 2;

FIG. 4 is a rear elevational view of a first insert in accordance with the embodiment of FIGS. 1-3;

FIG. 23 is a cross-sectional view of a support and a set of inserts in accordance with another embodiment of the invention.

DETAILED DESCRIPTION

Figure 5:
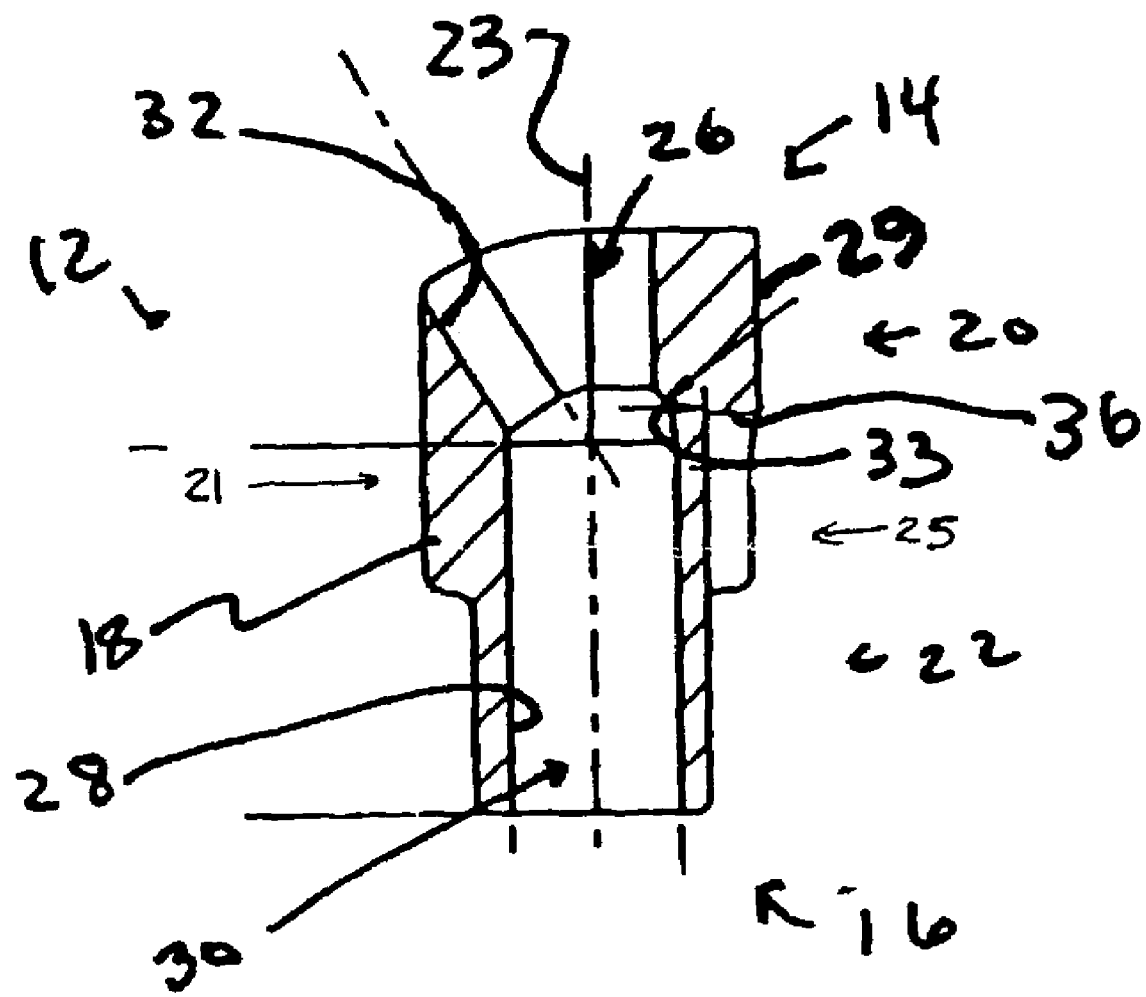
FIG. 5 is a cross-sectional view taken along line 5-5 in FIG. 4.
Figure 7:
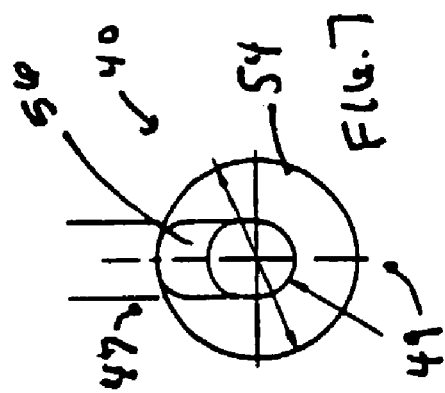
FIG. 7 is a top plan view of a second insert in accordance with the embodiment of FIGS. 1-6.
Figure 6:
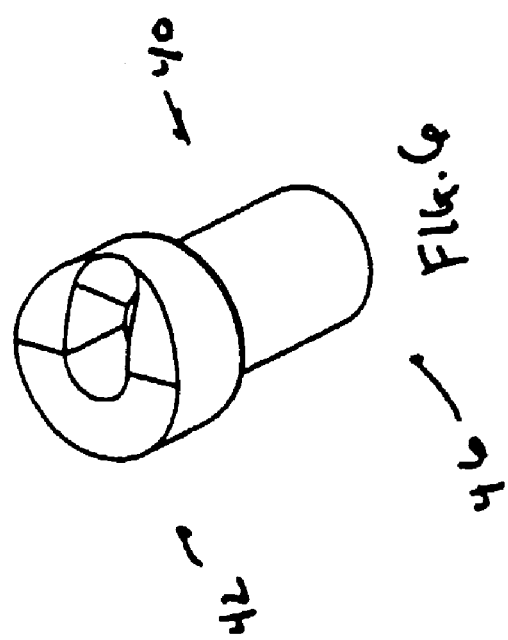
FIG. 6 is a top-right perspective view of a second insert in accordance with the embodiment of FIGS. 1-5.
Figure 8:
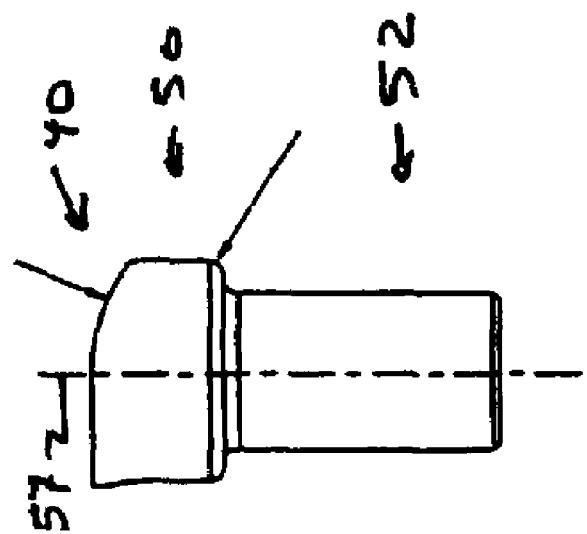
FIG. 8 is a left elevational view of a second insert in accordance with the embodiment of FIGS. 1-7.

FIGS. 1-22 show an embodiment of the present invention, in which an apparatus 10 includes a first insert 12. The first insert has a sidewall 18 forming a generally cylindrical body with an upper end 14, lower end 16, front 21, rear 25 and central axis 23, as best seen in FIG. 5. The body has an upper cylindrical portion 20 and a lower cylindrical portion 22, both centered on the axis 23. In the embodiment shown, the first insert 12 is cylindrical and has an upper cylindrical portion 20 with a greater diameter than the diameter of the lower cylindrical portion 22. However, the insert may have a variety of regular or irregular shapes.

Figure 2:
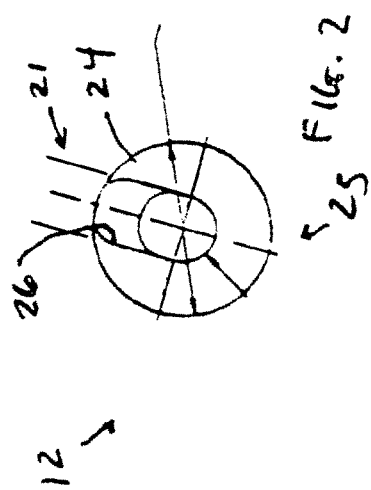
FIG. 2 is a top plan view of a first insert in accordance with the embodiment of FIG. 1.
Figure 1:
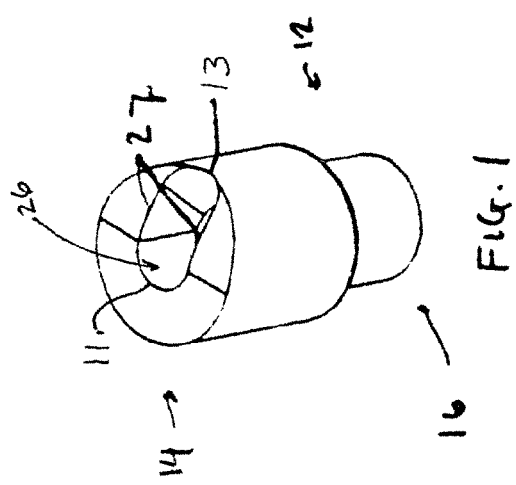
FIG. 1 is a top-right perspective view of a first insert in accordance with an embodiment of the invention.

As seen in FIG. 5, the wall 18 has an inner surface 28 defining a bore 30. The bore 30 is desirably open at the upper end 14 and lower end 16 of the first insert 12 and centered on the axis 23. In the embodiment shown, the first insert 12 includes a top wall 24 at the upper end 14, in which a slot 26 is defined. (FIGS. 1 and 2). The slot communicates with the bore 30. The slot 26 has an elongate shape extending from a first end 11 at the central axis 23 of the first insert 12 to a second end 13 at the front 21 of the first insert 12, as best seen in FIG. 1. The slot has edge surfaces 27 generally extending from the first end 11 to the second end 13.

The inner surface 28 includes an inclined surface 32 extending from the slot 26 at the front 21 of the first insert, toward the axis 23, as best seen in FIG. 5. The slot 26 and bore 30 are offset from one another at the rear 25 of the first insert. The inner surface 28 of the sidewall 18 forms an engagement surface 33 extending between the slot 26 and the bore 30 at the offset, at the rear 25 of the first insert. As shown in FIG. 5, the engagement surface 33 curves inwardly from the bore 30 to the slot 26.

An outer surface 29 of the sidewall 18 defines a notch 34 at the rear 25 of the first insert 12. The notch 34 extends from a stop 36 closing an upper end of the notch 34 to an open end at the lower end 16, as best seen in FIG. 4.

Figure 9:
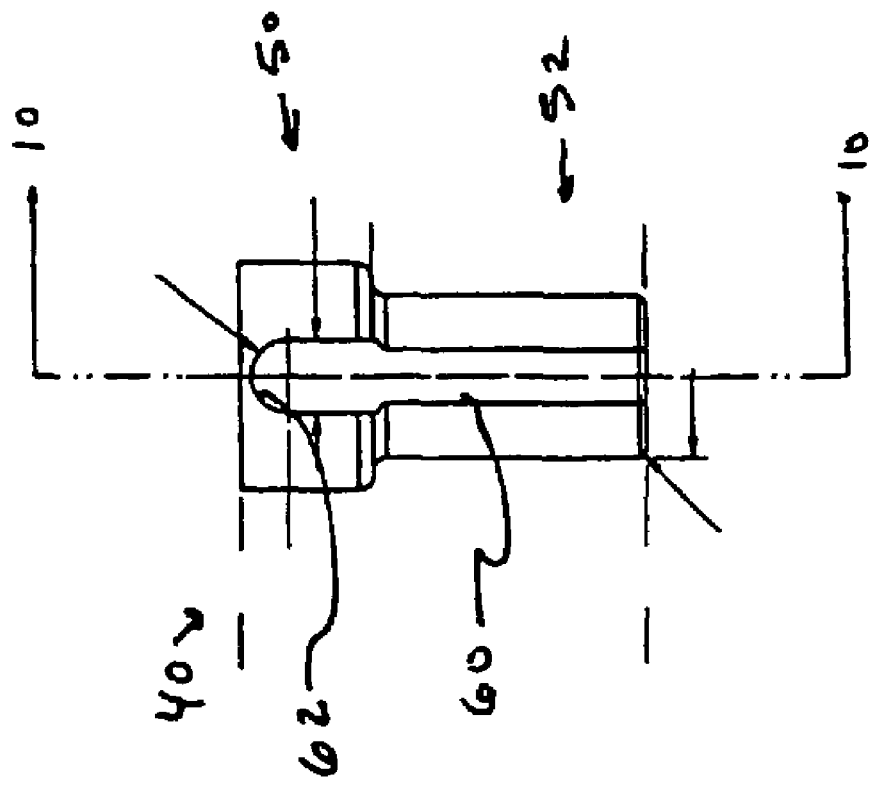
FIG. 9 is a rear elevational view of a second insert in accordance with the embodiment of FIGS. 1-8.
Figure 10:
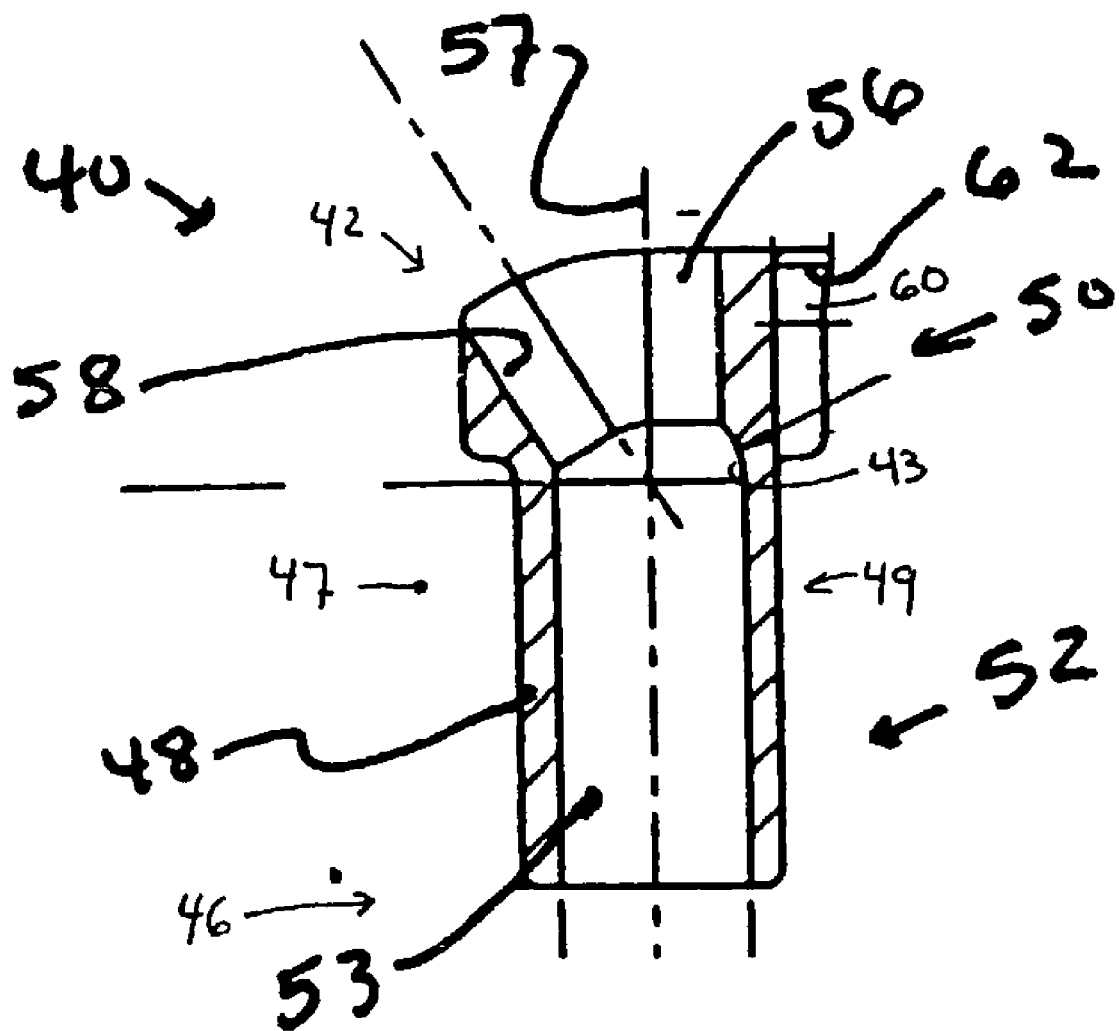
FIG. 10 is a cross-section taken along line 10-10 in FIG. 9.

A second insert 40, which is generally similar to the first insert, is shown in FIGS. 6-10. However, the second insert is shaped so as to be positioned at a different elevation with respect to the bone, as discussed further below. As best seen in FIG. 10, the second insert has a wall 48 forming a generally cylindrical body with an upper end 42, a lower end 46, a front 47, a rear 49 and a central axis 57. The wall 48 defines an upper cylindrical portion 50 and a lower cylindrical portion 52. In the embodiment shown, the second insert 40 is generally cylindrical, but may have other shapes. The second insert 40 and first insert 12 may have the same height or different heights. Preferably, the first insert 12 and second insert 40 have about the same radial dimensions. The second insert 40 has a bore 53 extending from the lower end 46 to a slot 56 in a top wall 54. The slot 56 has an elongate shape, extending from the central axis 57 to the outer surface of the wall 48, at the front 47 of the second insert 40. (FIGS. 7 and 10) The second insert has an inclined surface 58 at the front of the insert. As best seen in FIG. 9, a notch 60 is defined by the wall 48 at the rear 49 of the second insert 40. The notch 60 is open on the lower end 46 of the second insert 40 and extends from the lower end 46 to a stop 62.

The slot 56 and bore 53 are offset from one another at the rear 49. The second insert 40 has an engagement surface 43 extending between the slot 56 and the bore 53, at the rear 49, where the slot 56 and bore 53 are offset from one another. In the embodiment shown in FIGS. 5 and 10, the engagement surface 33 and engagement surface 43 have the same elevation on each insert. As seen in FIGS. 5 and 10, notch 34 and notch 60 have different elevations on each insert. Thus, the stop 36 is located closer to the engagement surface 33 on the first insert, as compared to the spacing of the stop 62 from surface 43.

Figure 11:
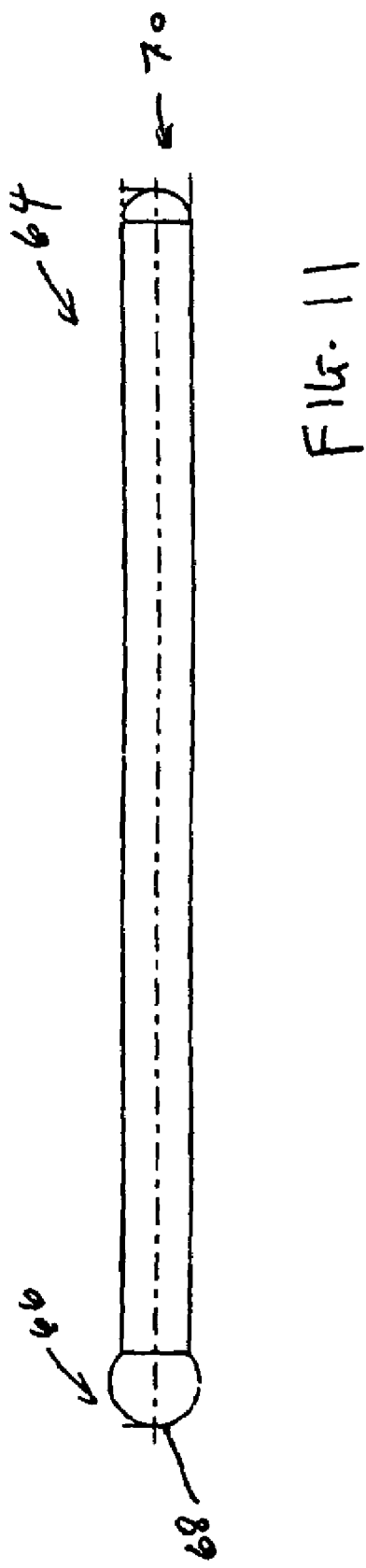
FIG. 11 is a front elevational view of a post in accordance with the embodiment of FIGS. 1-10.

In certain preferred embodiments, a post is assembled with each of the inserts 12 and 40. Each post may be as shown in FIG. 11. The post 64 comprises an elongate member having a first end 66 and a second end 70. The first end 66 is shaped for engaging the engagement surface on the insert and for allowing the post to pivot. Preferably, the first end 66 has a curved surface 68. However, the surface 68 of the post 64 may have a surface 68 with a variety of shapes. For example, the surface 68 may comprise a hemispherical surface, or another curved shape. Preferably, the engagement surface on the insert to be used with the post corresponds to the shape of the first end 66.

Figure 12:
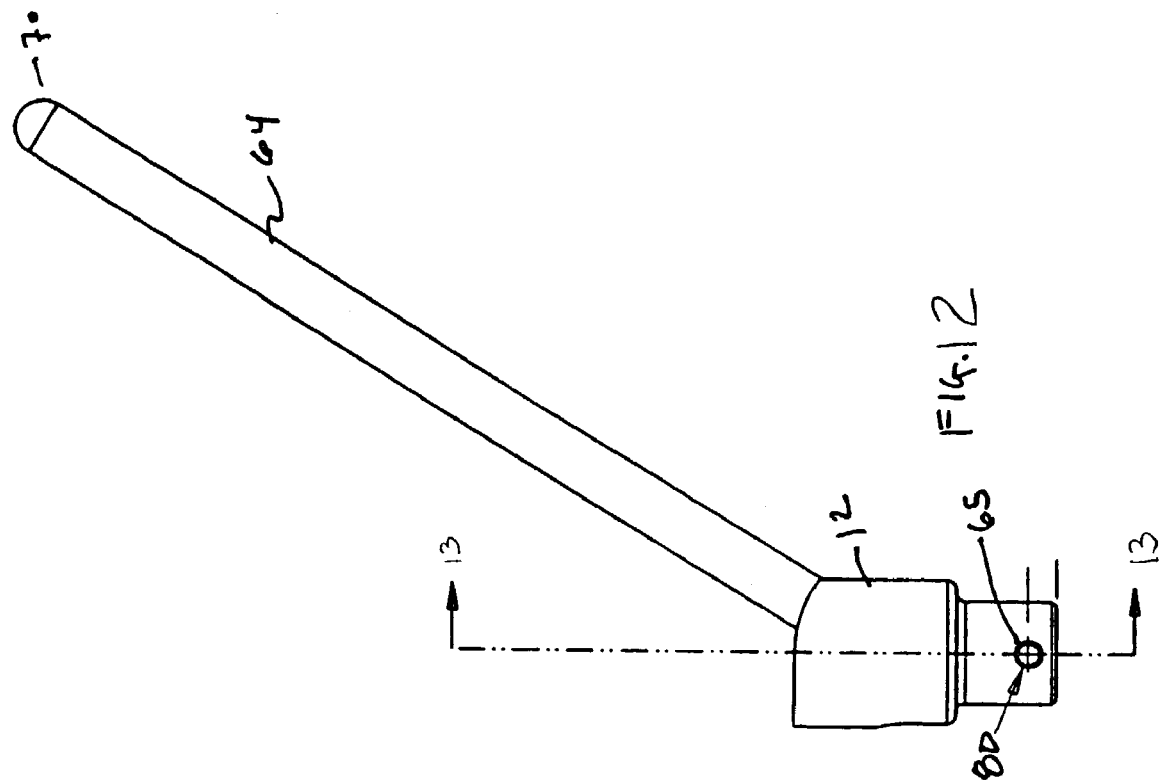
FIG. 12 is a left side elevational view of the post assembled with the first insert in accordance with the embodiment of FIGS. 1-11.
Figure 13:
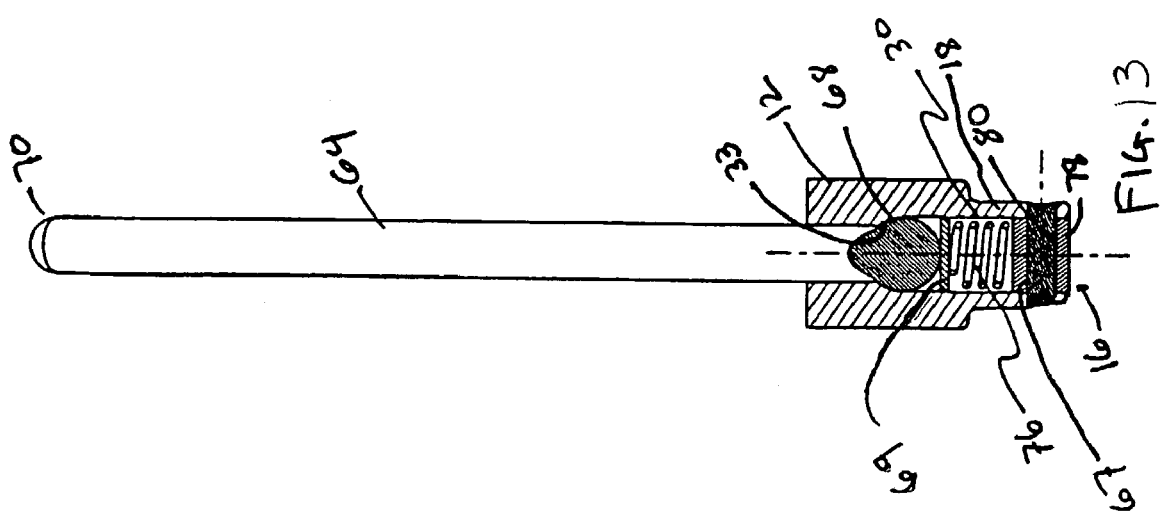
FIG. 13 is a cross-section taken along lines 13-13 in FIG. 12.

The post may be assembled with one of the inserts as follows. For example, a second end 70 of the post is inserted into the bore 30 of the first insert 12, at the lower end 16, and advanced into the bore 30. The second end 70 of the post passes through the slot 26. The post 64 is advanced into the bore 30 until the curved surface 68 engages the engagement surface 33 in the bore 30, as shown in FIG. 12. The post 64 is then fixed in the first insert 12 by any means known in the art. In certain embodiments, a washer 69 and a resilient element 76 is disposed in the bore 30 so as to engage the curved surface 68 and seat the first end 66 against the engagement surface. A cap 78 having a cylindrical shape corresponding to the bore 30 is inserted into the bore 30 so as to press the resilient element 76 against the curved surface 68 and is secured in the bore 30 to secure the resilient element 76 and post 64 in the first insert. One arrangement for securing the cap comprises a pin 80 in an aperture 65 extending laterally through the wall 18 of the first insert 12 and also through a hole 67 extending laterally through the cap 78, so that the pin 80 extends through the wall 18 and through the cap 78. However, any other arrangement may be used. For example, the cap 78 may be threadably received in the bore 30. In other embodiments, the bore 30 at the lower end 16 is closed and the first end 66 is inserted in the bore 30 at the upper end 14 and secured at the upper end 14.

Preferably, posts are preassembled with each of the inserts. However, the posts, inserts and other parts can be disassembled or otherwise arranged so that they can be adequately cleaned. The engagement surface 33 of the first insert 12 and engagement surface 43 of the second insert 40 are shaped to correspond to the shape of the curved surface 68 of the first end 66 of the post 64 and to allow the post to pivot. The slot 26 is arranged in the top wall 24 so that the pivoting of the post 64 is guided in the direction in which the slot 26 extends. The post 64 translates from a position generally in alignment with the central longitudinal axis of the insert to a position leaning toward the front of the insert, as shown in FIG. 12. For example, the first insert 12 has a slot 26 extending from the axis 23 to the front 21 of the insert. The inclined surface 32 defines the end of the slot 26 at the front 21 and the slot 26 has a rear end 13 arranged so as to position the post 64 substantially along axis 23, in a first position. The post 64 may be pivoted around the first end 66, as guided by the edge surfaces 27 of the slot 26 toward the front end 11 of the slot 26. At the front end 11, the post 64 has a second position in which the post 64 rests on the inclined surface 32.

The posts may be assembled on the inserts so that the posts are pivotable using any means known in the art. For example, the post and insert may have a hinged connection. The post may or may not have an end disposed in a bore in the insert. A portion of the post may be formed from a flexible material so that flexing of the post pivots the post with respect to the support.

Figure 14:
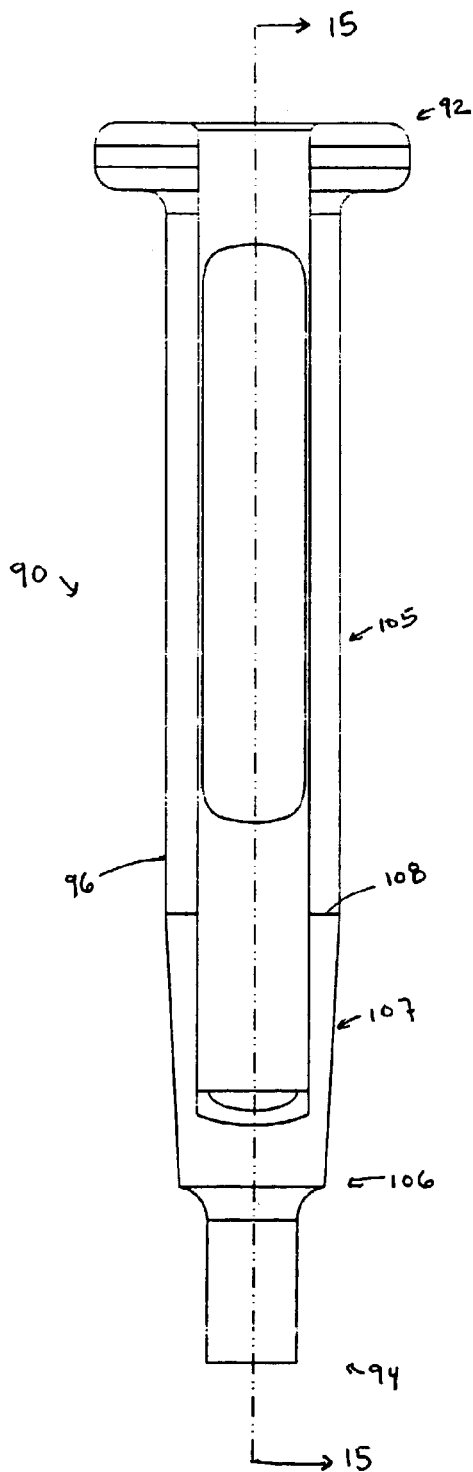
FIG. 14 is a front elevational view of a support in accordance with the embodiment of FIGS. 1-13.
Figure 16:
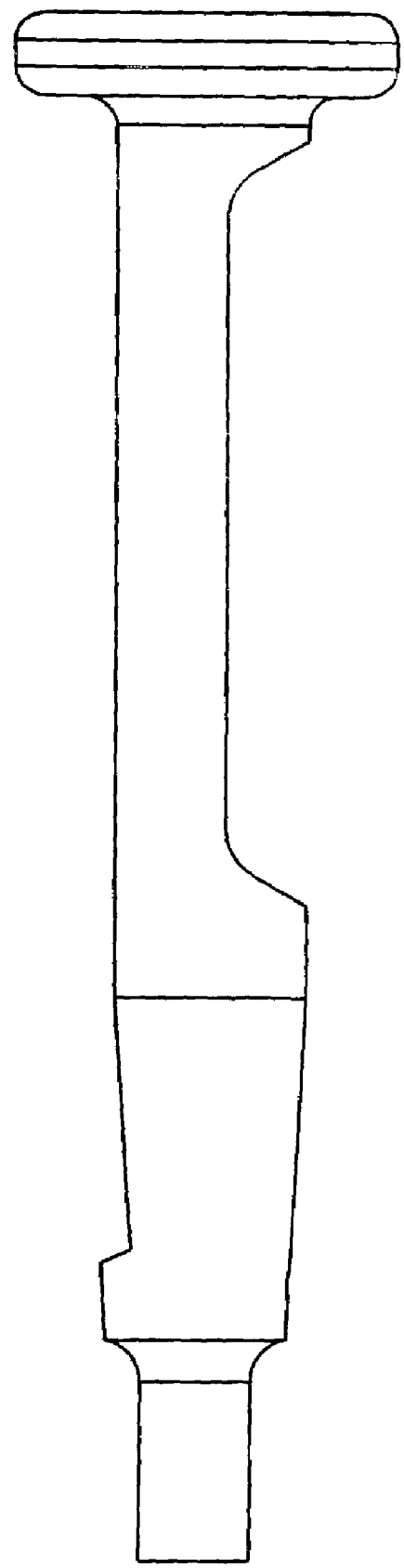
FIG. 16 is a right elevational view of a support in accordance with the embodiment of FIGS. 1-15.
Figure 17:
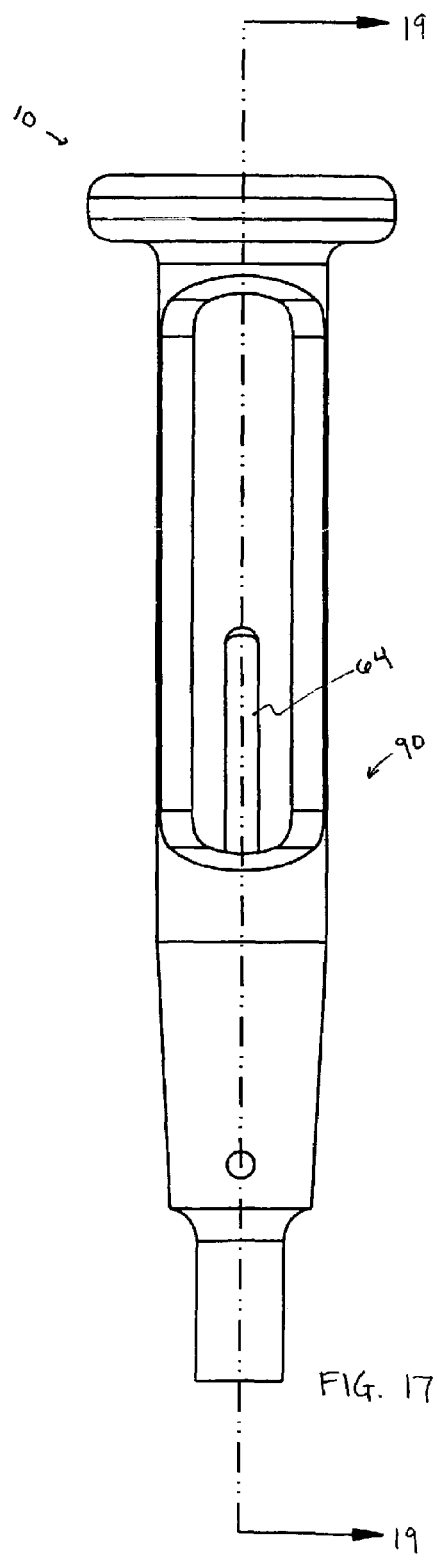
FIG. 17 is a rear elevational view of a support assembled with a second insert in accordance with the embodiment of FIGS. 1-16.
Figure 18:
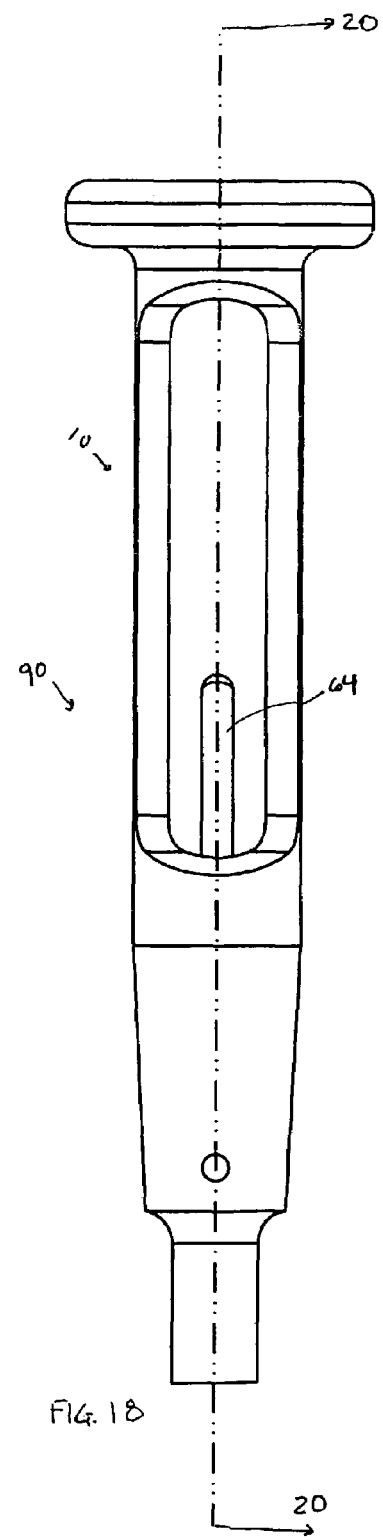
FIG. 18 is a rear elevational view of a support assembled with a first insert in accordance with the embodiment of FIGS. 1-17.

The apparatus 10 includes a support 90 having a body 96 with a front side 95, rear side 97, upper side 92 and lower side 94. (See FIGS. 14-16). The body has an elongate shape and extends from the upper side 92 to the lower side 94. The body 96 has an exterior surface 98 and an interior surface 100. The interior surface 100 defines a passage 102 that is open on the upper side 92 of the support 90. An opening 104 at the front side 95 of the body communicates with the passage 102, whereas the rear side 97 is closed. The support body 96 forms a cylindrical part 105 extending from the upper side 92 to a conical part 107 at the lower side 94. The opening 104 and passage 102 extend to the conical part, as best seen in FIG. 14. The conical part 107 has a frusto-conical shape, tapering toward the lower side 94 of the support 90. In other embodiments, the support may have other shapes.

Figure 15:
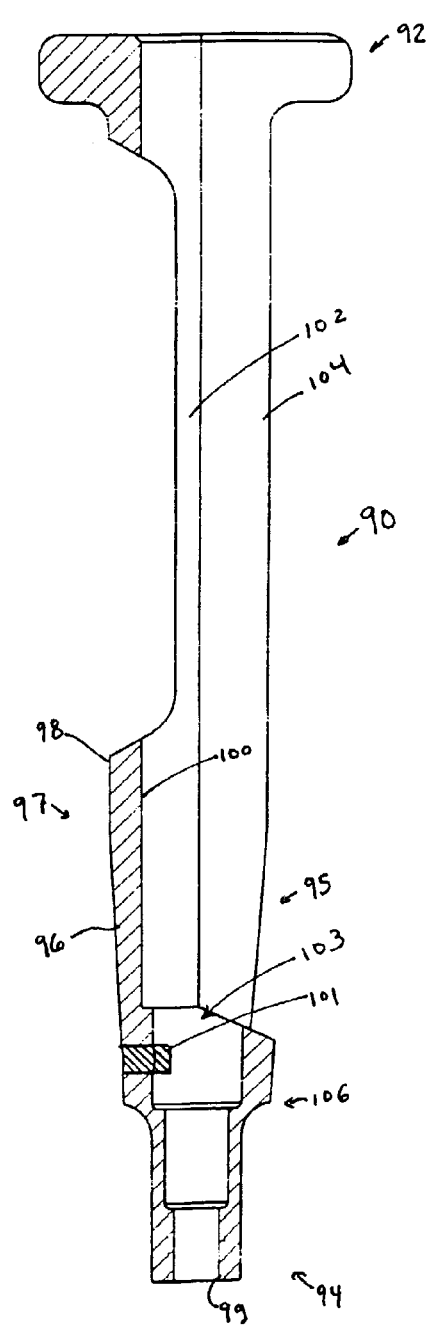
FIG. 15 is a cross-section taken along line 15-15 in FIG. 14.

The support 90 has a mounting portion 106 in the conical part 107. The passage 102 and opening 104 communicate with a cavity 103 in the mounting portion 106. The cavity 103 is sized and shaped for receiving the first insert 12 and second insert 40, or any number of inserts provided in a set. A protrusion 101 extends from the wall 96 at the rear side 97 into the cavity 103, as best seen in FIG. 15. The upper side 92 incorporates a flange extending radially outwardly from the wall 96. The flange is desirably arranged for mounting a handle or other instruments on the support. The lower side 94 is desirably arranged for connection with a stabilizing element. In the embodiment shown, the lower side 94 has a threaded bore 99 for connecting with the stabilizing element disposed in the bone. The stabilizing element may comprise a rod, stem, or any element disposed in or mounted on the bone.

The conical part 107 of the support 90 is shaped so as to be received in the cavity formed in the femur, at a predetermined elevation in the femur, seating the entire apparatus in the femur. The shape of the conical part 107 desirably corresponds to the shape, at the predetermined elevation, of the prosthesis to be implanted in the femur. Desirably, a tapered surface extends within the cavity in the femur so as to correspond to the prosthesis to be implanted, and the tapered shape of the conical part 107 seats the support in the recess. The support desirably includes a groove 108, or may include indicia, for confirming the position of the support 90 in the recess in the bone.

The support 90 may have a variety of shapes, including polygonal, curved, cylindrical, conical, and other regular or irregular shapes. The support 90 is desirably shaped to correspond approximately to the shape of the recess in the bone or at least to fit therein adequately so that the shaping of the bone can be accomplished as desired with the assembly.

The inserts are received in the cavity 103 of the support 90. For example, the first insert 12 is inserted in the cavity 103 of the mounting portion 106 with the rear 25 of the first insert 12 facing the rear side 97 of the support 90. As the notch 34 is formed in the wall 18 at the rear 25, and the protrusion 101 is formed at the rear side 97, the protrusion 101 is received in the notch 34. The slot 26 extends from the axis 23 to the front 21 of the first insert 12 so that, when the protrusion 101 is received in the notch 34, the slot 26 extends in a predetermined direction of the apparatus. The slot 26 is thereby located so that when the post 64 tilts toward the front 21 of the first insert 12, and the post 64 passes through the opening 104. The protrusion 101 and notch 34 also locate the post in elevation with respect to the bone, as the mounting portion 106 has a predetermined elevation in the bone, the protrusion 101 has a predetermined elevation with respect to the seat 106 and the notch 34 and curved surface 68 have a predetermined elevation on the first insert 12.

Figure 19:
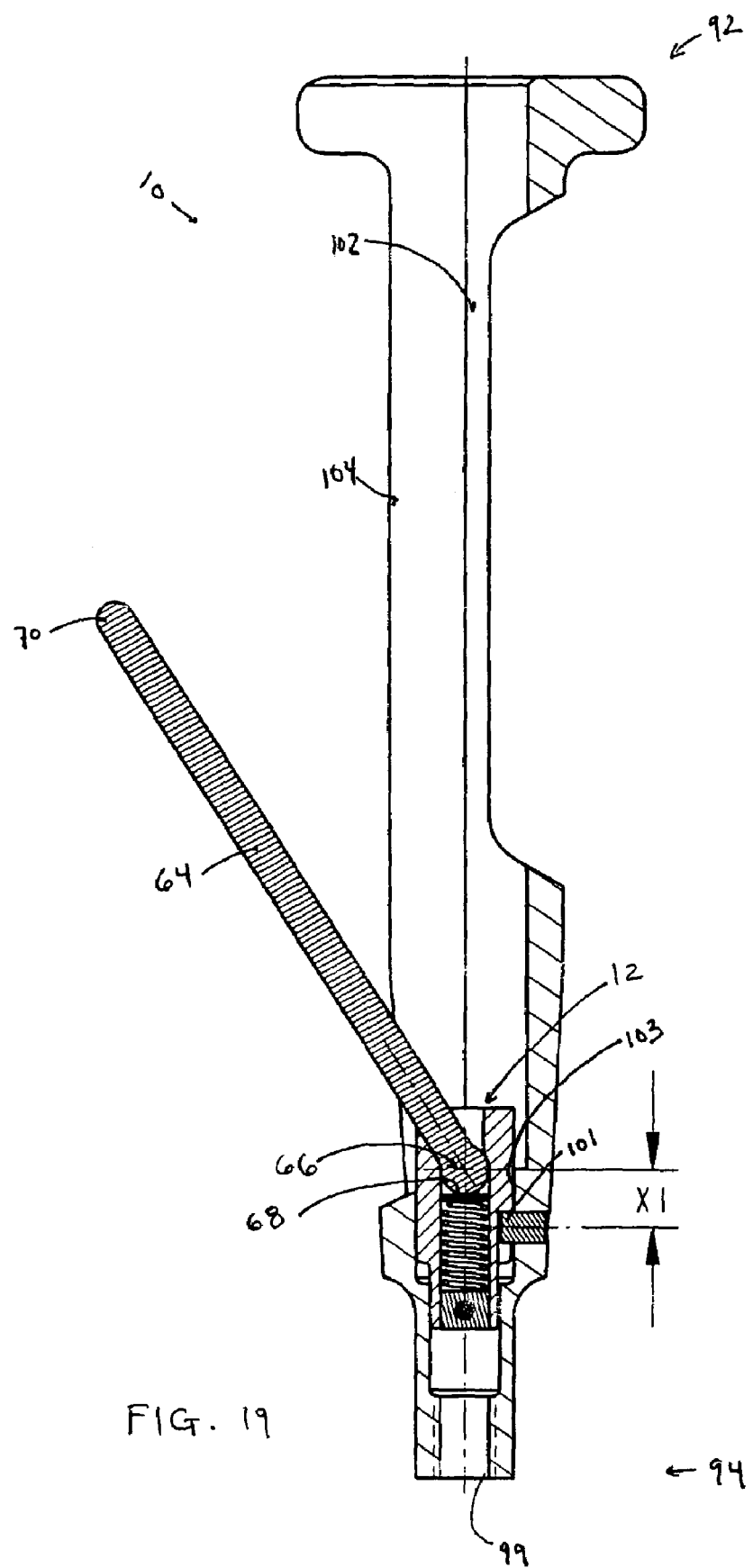
FIG. 19 is a cross-section taken along line 19-19 in FIG. 17.
Figure 20:
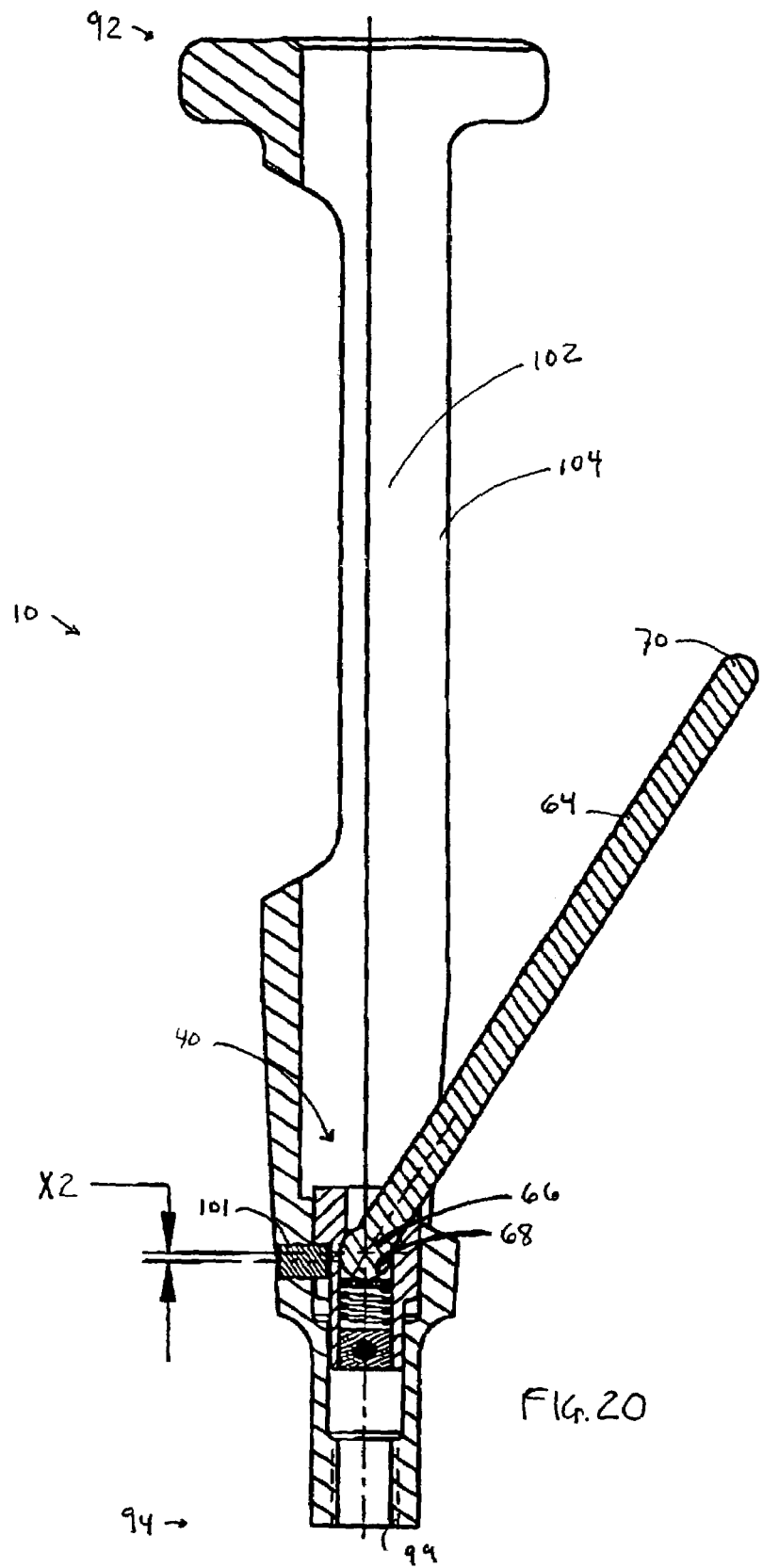
FIG. 20 is a cross-section taken along line 20-20 in FIG. 18.

As shown in FIGS. 19 and 20, the protrusion 101 in the support 90 locates the inserts in the support. The second insert 40 has the notch 60 at the rear 49 of the insert 40. Thus, the notch 60 is opposite the front 47 and the slot 56 extends generally between the rear 49 and the front 47 of the insert. The protrusion 101 is located at the rear side 97 of the support so that when the second insert 40 is inserted in the cavity 103 of the support 90 so that the notch 60 engages the protrusion 101, the slot 56 extends generally between the rear side 97 and the front side 95 of the support 90. As the opening 104 is located at the front side 95, a post 64 extends through the opening 104 when the post 64 has been pivoted so as to rest on the inclined surface 58 of the slot 56.

The second insert 40 has a notch 60 with a stop 62 at a predetermined position with respect to the top wall 54 of the second insert 40. The stop 62 engages protrusion 101 so that the center of the protrusion 101 is spaced from the center of the first end 66 by a distance X2, as shown in FIG. 20. The first insert 12 shown in FIG. 19 has the notch 34 with the stop 36 at a different position. The stop 36 engages the protrusion 101 so that the center of the protrusion 101 is spaced from the center of the first end 66 by a distance X1. As the distance X2 for the second insert 40 is different from the distance X1 for the first insert 12, the shaping tool has a different position with respect to the support.

Figure 21:
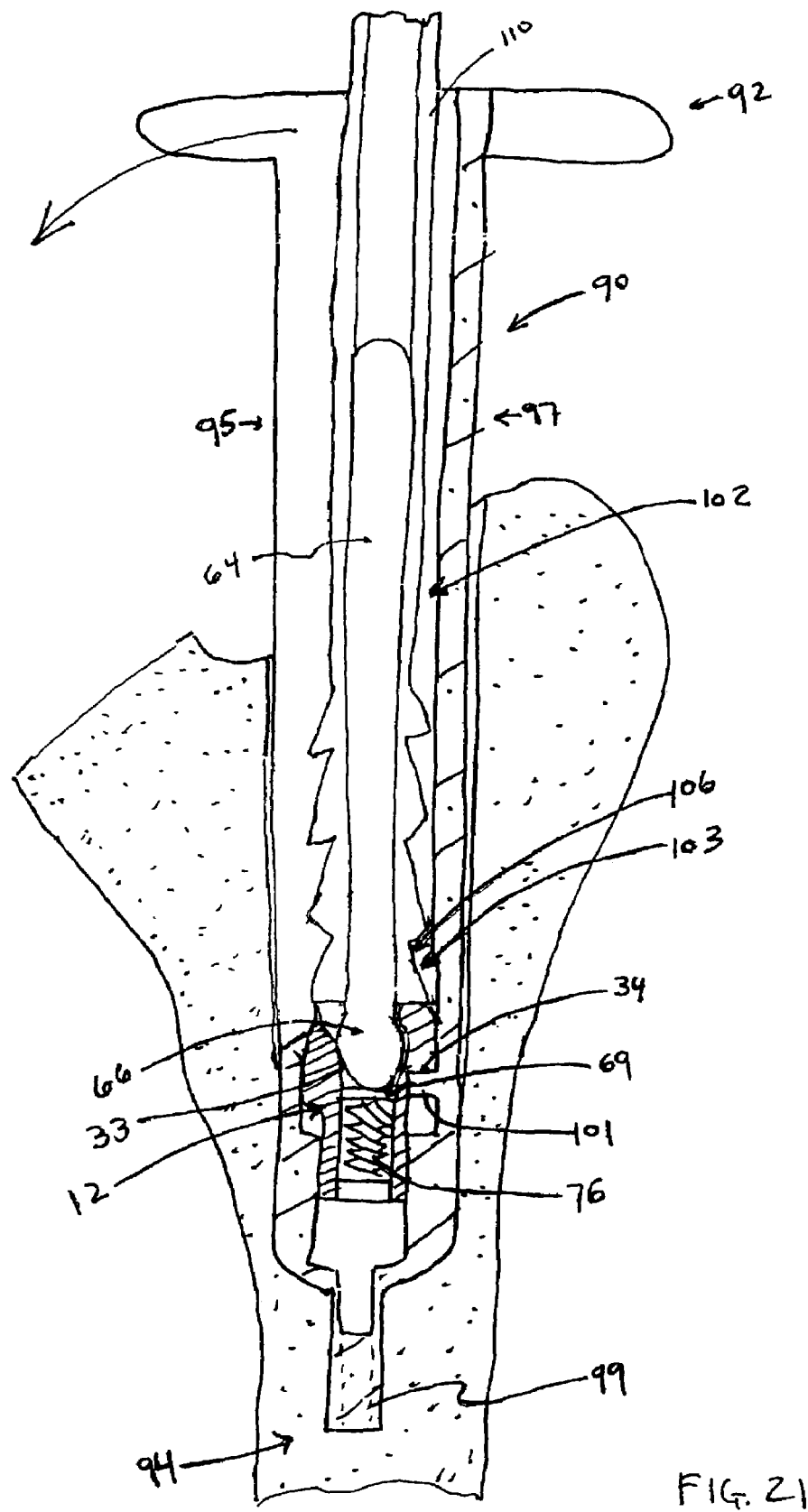
FIG. 21 is a cross-sectional view of a support, insert and shaping tool in a first position in accordance with the embodiment of FIGS. 1-20.
Figure 22:
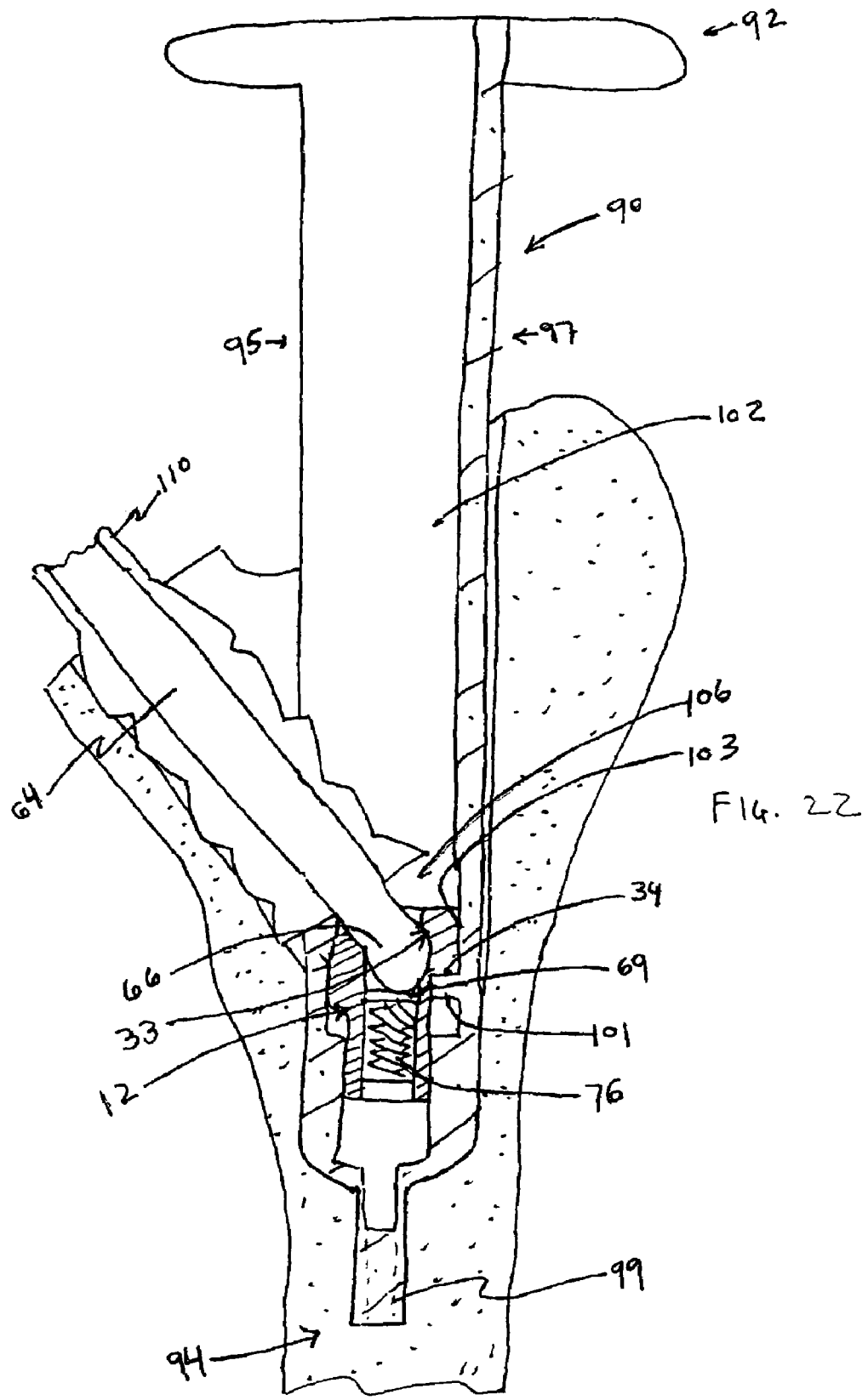
FIG. 22 is the cross-sectional view of FIG. 21 showing the shaping tool in a second position.

The apparatus desirably includes at least one shaping tool 110 for shaping the recess in the bone. The shaping tool 110 may comprise a reamer with an abrasive surface that may comprise cutting edges 112. The cutting edges in FIGS. 21 and 22 are helical in shape. However, other shapes may be used. The shaping tool 110 desirably has a top end 114 shaped for mating with a driver, which may comprise a manual or motorized driver. In further embodiments of the invention, the post has cutting features or abrasive features so that the post comprises a shaping tool.

The apparatus 10 desirably includes a set of instruments having a plurality of inserts for locating the post in a range of elevations in the femur with respect to the prosthesis to be implanted. After the surgeon has selected the prosthesis to be implanted, the cavity is formed in the bone by the surgeon. For example, the cavity may be formed using a conical reamer, for forming a cavity with a shape corresponding to the shape of the support and for locating the support in the bone. The conical reamer, or other reamer for forming the cavity includes indicia for indicating the depth of the cavity so that the prosthesis is property mounted in the cavity. The threaded bore 99 on the support 90 is used to connect the support 90 to a stabilizing element, such as a centralizing rod, and the stabilizing element is inserted into the elongated hole in the medullary portion of the bone. Other arrangements may be used to connect the stabilizing element and support 90, in the event such element is used, such as corresponding polygonal shapes on the stabilizing element and in the bore. The stabilizing element may comprise a part of the prosthesis to be implanted. In other embodiments, the stabilizing element comprises a portion of the support.

The insert corresponding to the prosthesis is selected by the surgeon and introduced into the cavity 103 of the guide body 90. The engagement of the protrusion 101 locates the insert accurately within the cavity 103, as discussed above. The support 90 is arranged so as to locate the slot on the insert so that the post extends out opening 104 of the support when pivoted, and at the correct elevation in the femur, once the support 90 is positioned in the cavity of the femur.

A shaping tool is then selected for shaping the cavity and the shaping tool is mounted on the post. For example, the shaping tool 110 comprises a reamer with a hole and the post is inserted into the hole in the shaping tool 110. Other arrangements for mounting the shaping tool on the post may be used. The engagement of the notch 34 and protrusion 101 ensures that the shaping tool has the desired elevation within the femur, so that the shaping tool 110 shapes the cavity for the prosthesis selected by the surgeon. The end 114 of the shaping tool 110 is connected to a driver, for either manual or mechanically driven rotation of the shaping tool. The shaping tool 110 is simultaneously pivoted, pivoting the post 64 and the shaping tool 110 installed on the post. (FIGS. 21 and 22) The shaping tool 110 is arranged to form the appropriately sized cavity within the proximal portion of the femur for the prosthesis already selected by the surgeon.

Thus, each insert corresponds to a prosthesis that may be selected from a set of prostheses. As several inserts may be assembled with the support, the inventory for the set of instruments is reduced.

The support may comprise any suitable support for the insert and for being received in the cavity of the bone. For example, the support may comprise a part of the prosthesis to be implanted, or any other orthopedic device.

In further embodiments of the invention, the inserts have shapes other than cylindrical shapes. The inserts may have any polygonal or curvilinear shape. In addition, the support may be arranged so as to receive the inserts from a lower end of the support. In certain embodiments, the shape of the insert locates the position of the post and shaping tool in elevation. For example, the insert may have a tapered shape, in the direction toward the lower end. The radial dimensions of each insert may determine the elevation of the insert with respect to the bone, when mounted on the support. In other embodiments, the insert may have a flange that engages a ledge within the cavity so as to locate the post. In certain embodiments, the shape of the insert locates the post and shaping tool for pivoting in a predetermined direction of the bone, such as a polygonal insert received in a polygonal cavity in the support. In addition, in other embodiments, a further element may engage the support and insert so as to locate the post. In other embodiments, the insert is threadably received in the cavity of the body. In further embodiments, the cavity in the support may be omitted and the inserts and support may be assembled with each other by other means. For example, the inserts may include a cavity for receiving a portion of the support.

The insert may be shaped for connecting to a reamer or other shaping tool, and the post may be omitted. The post may be connected to the insert using any suitable mechanical arrangement. The insert may have a connecting portion received by the reamer, for example.

In a further embodiment of the invention, each insert from a set of inserts has a feature that engages the support and which is located in the same position on all the inserts in the set. As shown in FIG. 23, each insert 212a, 212b, 212c has an engagement surface 233a, 233b, 233c with a different position in elevation from the other inserts. Each insert has an upper end 214a, 214b, 214c that abuts a flange 201 on the support 290. The inserts are received at a lower end of the cavity 203 in the support 290. The inserts desirably carry a resilient element 276 for biasing the end of the rod against the engagement surface, seating the rod. A threaded cap 278, or other feature, is used to secure the insert and resilient element in the insert. In other embodiments, the inserts and support are shaped so that the shaping tool is positioned at the same elevation, but different positions with respect to the recess, in some other respect.

Although the invention herein has been described with reference to particular embodiments, it is to be understood that these embodiments are merely illustrative of the principles and applications of the present invention. For example, the specific embodiments discussed above are directed to shaping the femoral bone. However, embodiments of the present invention include instruments for shaping bones other than the femur. It is therefore to be understood that numerous modifications may be made to the illustrative embodiments and that other arrangements may be devised without departing from the spirit and scope of the present invention as defined by the appended claims.

The invention claimed is:

1. An apparatus for shaping a bone, comprising:
a) an insert for guiding pivoting of a shaping tool;
b) a support having an end adapted to be inserted in a cavity in the bone and having a mounting portion including means for mounting the insert on the support and preventing the insert from rotating therein during pivoting of the shaping tool; and
c) a post for pivotally engaging with the insert for guiding pivoting of a shaping tool,
wherein the post is assembled within the insert, the insert having a central axis, and the post being pivotable, with respect to the insert central axis between a first position and a second position.

2. The apparatus of claim 1, wherein the insert is arranged to guide pivoting in a predetermined direction with respect to the bone.

3. The apparatus of claim 2, wherein the insert has a connecting portion for connecting with the shaping tool.

4. The apparatus of claim 3, wherein the connecting portion comprises the post assembled with the insert.

5. The apparatus of claim 4, wherein the insert has a bore defined therein, the bore being open on an upper end and a lower end of the first insert and incorporating an engagement surface for engaging an end of the post, the post being received in the bore so that the post extends out the bore at the upper end of the insert.

6. The apparatus of claim 1, wherein the post is assembled with the insert and wherein the insert has a surface for guiding pivoting of the shaping tool.

7. The apparatus of claim 1, wherein the insert has a top wall and a slot defined in the top wall, the insert having a sidewall defining a bore in communication with the slot.

8. The apparatus of claim 7, wherein the insert has a central axis and the bore is centered on the central axis.

9. The apparatus of claim 8, wherein the slot extends in the top wall from the central axis to the sidewall of the insert.

10. The apparatus of claim 9, wherein the slot and the bore are offset from one another at a location and the bore has an engagement surface that extends between the slot and the bore at the location of the offset.

11. The apparatus of claim 10, wherein the insert has a connecting portion comprising the post having an end with a shape corresponding to the shape of the engagement surface.

12. The apparatus of claim 11, further comprising a fixing element for securing the end of the post in the insert.

13. The apparatus of claim 1, wherein the insert comprises a first insert of a plurality of inserts, the first insert being shaped for mounting on the support and for positioning the first insert with respect to the support.

14. The apparatus of claim 13, further comprising a second insert, the first insert and the second insert being shaped for mounting with the support so that a shaping tool connected to the first insert has a position with respect to the support that is different from the shaping tool connected to the second insert.

15. The apparatus of claim 1, wherein the support comprises a body and the mounting portion of the support comprises a cavity defined by the body for receiving the insert.

16. The apparatus of claim 15, wherein the body of the support has a longitudinally extending passage communicating with the cavity and defining an opening so that the passage is open at a front side of the support, so that the shaping tool may extend out the opening.

17. The apparatus of claim 16, wherein the insert and the support are shaped for positioning the insert and the shaping tool with respect to the support.

18. The apparatus of claim 1, wherein the support has an upper cylindrical portion and a lower conical portion.

19. The apparatus of claim 18, wherein the lower conical portion is shaped to correspond to a portion of a prosthesis to be inserted in the cavity and the conical portion of the support positions the support within the bone.

20. The apparatus of claim 19, wherein the lower end of the support is shaped to be received in a cavity in a proximal end of a femur.

21. The apparatus of claim 1, wherein the insert and the support are shaped for locating the insert at a predetermined elevation with respect to the bone.

22. The apparatus of claim 1, wherein the insert and the support are shaped for locating the insert with respect to the bone so that the shaping tool pivots in a predetermined direction.

23. The apparatus of claim 1, wherein the post is assembled with the insert and further comprising a shaping tool shaped so as to be mounted on the post and to allow the shaping tool to rotate on the post.

24. The apparatus of claim 23, wherein the shaping tool comprises a reamer.

25. The apparatus of claim 1, wherein the means for mounting the insert is a protrusion extending into an insert receiving cavity in the mounting portion and engaging a recess in the insert.

26. A set of instruments for shaping a bone, comprising:
a) a support for being mounted in a cavity of the bone, the support having a mounting portion including means for mounting an insert on the support and preventing the insert from rotating therein during pivoting of the shaping tool;
b) a first insert for guiding pivoting of a shaping tool;
c) a second insert for guiding pivoting of a shaping tool;
d) the first insert and the second insert being shaped for engagement with the support so that the first insert and second insert have different positions with respect to the bone, wherein each insert is pivotally engaged with a post for relative movement therebetween in a direction transverse to a central axis of the insert for guiding pivoting of a shaping tool.

27. An apparatus for shaping a bone, comprising:
a) an insert shaped for guiding pivoting of a shaping tool; and
b) a support having an end adapted to be inserted in a cavity in the bone and having a mounting portion for mounting the insert on the support, wherein the insert is arranged to guide pivoting in a predetermined direction with respect to the bone, the insert has a connecting portion for connecting with the shaping tool, the connecting portion comprises a post assembled with the insert, and the insert has a bore defined therein, the bore being open on an upper end and a lower end of the insert and incorporating an engagement surface for engaging an end of the post, the post being received in the bore so that the post extends out the bore at the upper end of the insert.

28. An apparatus for shaping a bone, comprising:
a) an insert shaped for guiding pivoting of a shaping tool and
b) a support having an end adapted to be inserted in a cavity in the bone and having a mounting portion for mounting the first insert on the support, wherein the insert has a top wall and a slot defined in the top wall, the insert having a sidewall defining a bore in communication with the slot, the insert has a central axis and the bore is centered on the central axis, the slot extends in the top wall from the central axis to the sidewall of the insert, and the slot and the bore are offset from one another at a location and the bore has an engagement surface that extends between the slot and the bore at the location of the offset.

29. A method of shaping a bone, comprising the steps of:
a) selecting an insert from a set of a plurality of inserts
b) assembling the insert within a support, the insert being engaged with a post for guiding pivoting of a shaping tool, and the support including means to prevent the insert from rotating therein during pivoting of the shaping tool; and
c) inserting the support into a cavity in the bone either before or after assembling the support and the insert so as to position the shaping tool with respect to the bone.

30. The method of claim 29, wherein the insert is selected according to a desired position for shaping the bone, each of the inserts of the plurality of inserts arranged so as to locate the shaping tool in a different position when the support is mounted in the cavity of the bone.

31. The method of claim 29, further comprising selecting the insert according to a desired elevation, each of the inserts being arranged so as to locate the shaping tool in a different elevation with respect to the bone.

32. The method of claim 29, wherein the support is shaped so as to locate the support at a desired elevation with respect to the bone for shaping the bone for a preselected prosthesis.

33. The method of claim 29, further comprising positioning the insert with respect to the support so that the shaping tool pivots in a predetermined direction.

34. The method of claim 33, wherein the insert and the support are positioned by adjusting the position of the insert with respect to the support until correspondingly shaped features of the insert and support can be assembled with one another.

35. The method of claim 33, further comprising shaping the bone by pivoting the shaping tool in a predetermined direction of the bone, the insert being shaped to guide the pivoting of the shaping tool.

36. The method of claim 35, wherein the step of shaping includes rotating the shaping tool so as to engage cutting surfaces of the shaping tool with the bone.

37. The method of claim 33, further comprising rotating the support with respect to the bone to position the shaping tool.

38. The method of claim 37, wherein the support is positioned with respect to the bone so that the shaping tool engages a desired portion of the bone.

39. The method of claim 29, wherein the means for mounting the insert is a protrusion extending into an insert receiving cavity in the mounting portion and engaging a recess in the insert.

* * * * *